(12) United States Patent
Wang et al.

(10) Patent No.: US 9,746,404 B2
(45) Date of Patent: Aug. 29, 2017

(54) INSPECTION METHODS AND APPARATUSES FOR LIQUIDS

(71) Applicant: NUCTECH COMPANY LIMITED, Beijing (CN)

(72) Inventors: Hongqiu Wang, Beijing (CN); Yumin Yi, Beijing (CN); Huacheng Feng, Beijing (CN); Rui Fan, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 122 days.

(21) Appl. No.: 14/576,660

(22) Filed: Dec. 19, 2014

(65) Prior Publication Data
US 2015/0185130 A1    Jul. 2, 2015

(30) Foreign Application Priority Data

Dec. 27, 2013   (CN) .......................... 2013 1 0741358

(51) Int. Cl.
*G01N 21/00* (2006.01)
*G01N 5/00* (2006.01)
(Continued)

(52) U.S. Cl.
CPC .............. *G01N 5/00* (2013.01); *G01G 17/04* (2013.01); *G01N 21/3577* (2013.01); *G01N 21/65* (2013.01); *G01J 3/44* (2013.01)

(58) Field of Classification Search
CPC .................................................. G01N 21/65
See application file for complete search history.

(56) References Cited

U.S. PATENT DOCUMENTS 5,123,738 A * 6/1992 Yonemura .......... G01N 21/4785
                                                356/243.2
5,288,646 A * 2/1994 Lundsgaard ........... G01N 21/03
                                                356/246
(Continued)

FOREIGN PATENT DOCUMENTS

CN      101403711 A      4/2009
CN      102095666 A      6/2011
(Continued)

OTHER PUBLICATIONS

European Search Report dated Jul. 9, 2015 in corresponding European Patent Application No. 14 19 9253.
(Continued)

*Primary Examiner* — Kara E Geisel
*Assistant Examiner* — Rufus Phillips
(74) *Attorney, Agent, or Firm* — Pillsbury Winthrop Shaw Pittman LLP

(57) ABSTRACT

A method and apparatus for inspection of liquids are disclosed. The method includes inspecting a liquid with a technique selected according to whether the package of the liquid is transparent, semi-transparent or opaque. If the package is transparent or semi-transparent, a Raman spectra technique is used; if the package is opaque, a technique using an electronic scale and a barcode reader is used. In some embodiments, the Raman spectra technique and the technique using barcode reader and electronic scale can be used independently for inspection of the liquid. The inspection apparatus according to the present disclosure has advantages, such as capability of material identification, rapid examination speed, small volume, light weight, portability, low cost, freedom from radiation, and simple maintenance. The method and apparatus according to the present disclo-
(Continued)

sure are suitable for safety inspection in public places having a large number, and fast flow, of people.

20 Claims, 2 Drawing Sheets

(51) Int. Cl.
*G01N 21/3577* (2014.01)
*G01N 21/65* (2006.01)
*G01G 17/04* (2006.01)
*G01J 3/44* (2006.01)

(56) References Cited

U.S. PATENT DOCUMENTS

| | | | | |
|---|---|---|---|---|
| 5,523,845 | A * | 6/1996 | Honzawa | G01N 21/15 250/227.23 |
| 6,431,450 | B1 * | 8/2002 | Lundahl | G06K 7/10693 198/804 |
| 7,692,776 | B2 * | 4/2010 | Treado | G01J 3/02 356/301 |
| 7,748,623 | B2 * | 7/2010 | Barber | G06Q 10/00 235/375 |
| 8,248,600 | B2 * | 8/2012 | Matousek | G01J 3/44 356/301 |
| 2014/0010346 | A1 | 1/2014 | Chen et al. | |

FOREIGN PATENT DOCUMENTS

| | | |
|---|---|---|
| CN | 102507532 A | 6/2012 |
| CN | 203929643 U | 11/2014 |
| EP | 2 348 303 | 7/2011 |
| JP | 2007-248222 | 9/2007 |
| JP | 2009-251828 | 10/2009 |
| WO | 2008/062185 | 5/2008 |
| WO | 2008/075511 | 6/2008 |

OTHER PUBLICATIONS

Michael L. Ramirez et al., "Detection of Hazardous Liquids Concealed in Glass, Plastic and Aluminum Containers," Proc. of SPIE, vol. 6538, pp. 653827-1-653827-9 (2007).
Paul W. Loeffen et al., "Spatially Offset Raman Spectroscopy (SORS) for Liquid Screening," Proc. of SPIE, vol. 8189, pp. 81890C-1-81890C-10 (2011).
I.R. Lewis et al., "Raman spectroscopic studies of explosive materials: towards a fieldable explosives detector," Spectrochimica Acta Part A, vol. 51, pp. 1985-2000 (1995).
First Office Action as issued in Chinese Patent Application No. 201310741358.5, dated Nov. 28, 2016.
"The Liquid Explosive Security Equipment and Technology Development at Home and Abroad," Police Technology, Nov. 30, 2010, pp. 50-53.
Wang, Hong-qiu, et al., "Application of Raman Spectroscopy in Security Inspection," The Journal of Light Scattering, vol. 24, No. 4, Dec. 2012, pp. 367-370.

* cited by examiner

INSPECTION METHODS AND APPARATUSES FOR LIQUIDS

This application claims priority to Chinese patent application no. 201310741358.5, filed Dec. 27, 2013, which is incorporated herein in its entirety by reference.

TECHNICAL FIELD

Embodiments of the present disclosure relate to safety inspection technology, and more particularly, to methods and apparatuses for rapid safety inspection of liquids.

BACKGROUND

In recent years, terrorists have carried out violent terrorism activities in public places in various manners. A variety of dangerous liquids, such as dangerous chemicals, have been used in these terrorism activities. Safety inspection of liquids carried by people is specifically required in addition to general inspection of luggage or packages. The flow of people in public places is in huge quantity at high speed, and thus it requires a rapid and efficient method and apparatus for safety inspection.

SUMMARY

There are currently four types of methods for safety inspection of liquids, including the chemical method, electromagnetic method, neutron method and X-ray method as described below.

1) The chemical method includes methods like scent identification, ion scanning detection, and material analysis. The scent identification method is often ineffective in practical application because the liquid is sealed in a package. The ion scanning detection method is characterized by high sensitivity, but has a shortcoming of a high false alarm rate and susceptibility to influence from the background environment. The material analysis method has high precision and accuracy, but takes an amount of time for analyzing sample. Further, the method may cause chemical contamination. Therefore, the method may not meet the requirements of rapid inspection at a site.

2) The electromagnetic method uses active measurement, and distinguishes among different liquids based on permittivity of the liquids with respect to electromagnetic waves. The method is susceptible to adverse influence from, for example, a metallic package, a thick package material, and/or an irregularly-shaped package (e.g., bottle). Thus, use of the method is limited to the case of complicated package material.

3) Utilization of the neutron method will cause a phenomenon called "neutron activation." That is, there will be radiation residua in the liquid after inspection by the method. Meanwhile, neutrons have a strong penetrating power, and thus this method involves complicated radiation shield measurement. Further, the device may have a large footprint, and so may not be portable, and thus not suitable for use in most public places.

4) The X-ray method can be divided into 2-Dimensional (2D) X-ray scanning technology and CT technology. The general 2D scanning technology is mainly used for inspection of luggage, and unable to determine whether a liquid is dangerous. The CT technology has an advantage of not being affected by package material. Although it can perform liquid inspection, it requires shielding from rays. The imaging system, including the one or more X-ray sources and detectors, is large in volume and weight, not portable, expensive, and relatively slow in examination speed. It is difficult to be widely utilized.

The above four methods each have one or more disadvantages in terms of rapid safety inspection of liquids. A technique is needed for rapid inspection of liquids.

In view of one or more problems with conventional technology, embodiments of the present disclosure provide methods and apparatuses for inspection of liquids.

According to an aspect of the disclosure, there is provided a method of inspection of liquid, the method comprising: determining whether a package of a liquid is transparent, semi-transparent or opaque; if the package of the liquid is transparent or semi-transparent, directing a laser-emitting end of a Raman spectra module at the transparent or semi-transparent package of the liquid, operating to emit a laser beam, performing Raman spectra analysis on the liquid, and comparing Raman spectra information of the liquid with standard Raman spectra information of the liquid in a database to obtain an analysis result of the liquid and identify material of the liquid; if the package of the liquid is opaque, placing the liquid on an electronic scale to obtain weight information of the liquid, reading barcode information of the liquid with a barcode reader, retrieving standard weight information for the liquid from a database based on the read barcode information, and comparing the weight information from the electronic scale with the standard weight information from the database to determine whether the liquid is dangerous or suspicious.

In an embodiment, the liquid is determined to be dangerous or suspicious if a difference between the weight information and the standard weight information is larger than a first preset threshold.

In an embodiment, if the package of the liquid is opaque and has been opened, the method further comprises: taking part of the liquid and putting it into a transparent package; directing the laser-emitting end of the Raman spectra module at the transparent package, operating to emit a laser beam to perform Raman spectra analysis on the part of the liquid; and comparing Raman spectra information of the part of the liquid with the standard Raman spectra information of the liquid in the database to obtain an analysis result of the liquid.

In an embodiment, if a difference between the Raman spectra information of the liquid and the standard Raman spectra information is larger than a second preset threshold, the liquid is determined to be dangerous or suspicious, and the material of the liquid is identified.

According to another aspect of the disclosure, there is provided an apparatus for inspection of liquid, the apparatus comprising: an electronic scale that measures weight of a liquid under inspection; a barcode reader that reads barcode information of the liquid; a Raman spectra module that examines the liquid when a package of the liquid is transparent, semi-transparent or opaque; and a computer data processor coupled with the electronic scale, the barcode reader and the Raman spectra module and configured to retrieve standard weight information of the liquid from a database based on the read barcode information, and compare the weight information from the electronic scale with the standard weight information from the database to determine whether the liquid is dangerous or suspicious, or compare Raman spectra information of the liquid obtained by the Raman spectra module with standard Raman spectra information of the liquid in a database to obtain an analysis result of the liquid.

In an embodiment, the Raman spectra module comprises: a laser that emits laser to irradiate the liquid and generate Raman spectra; a spectrometer that receives the Raman spectra of the liquid; and an optical path module coupled between the laser and the spectrometer and configured to split the optical path, cause the laser arrive at the liquid, and transmit the Raman spectra back to the spectrometer.

In an embodiment, the liquid is determined to be dangerous or suspicious if a difference between the weight information and the standard weight information is larger than a first preset threshold.

In an embodiment, if a difference between the Raman spectra information of the liquid and the standard Raman spectra information is larger than a second preset threshold, the liquid is determined to be dangerous or suspicious, and the material of the liquid is identified.

In an embodiment, the optical path module comprises a probe with or without optical fiber.

In an embodiment, there are one or more lasers, spectrometers or optical path modules in the Raman spectra module.

In an embodiment, the electronic scale comprises one or more weighing sensors.

In an embodiment, there are one or more barcode readers, and if there are a plurality of barcode readers, the barcode readers are provided in a uniform or non-uniform arrangement.

In an embodiment, the computer data processor comprises a PC or an embedded processing unit.

In an embodiment, the computer data processor performs the comparison using a predefined recognition algorithm.

According to a further aspect of the disclosure, there is provided an apparatus for inspection of liquid, the apparatus comprising: an electronic scale that measures weight of a liquid under inspection; a barcode reader that reads barcode information of the liquid; and a computer data processor coupled with the electronic scale and the barcode reader, and configured to retrieve standard weight information of the liquid from a database based on the read barcode information, and compare the weight information from the electronic scale with the standard weight information from the database to determine whether the liquid is dangerous or suspicious.

According to a further aspect of the disclosure, there is provided an apparatus for inspection of liquid, the apparatus comprising: a Raman spectra module that examines the liquid when a package of the liquid is transparent, semi-transparent or opaque; and a computer data processor coupled with the Raman spectra module and configured to compare Raman spectra information of the liquid obtained by the Raman spectra module with standard Raman spectra information of the liquid in a database to obtain an analysis result of the liquid.

The inspection apparatus according to the present disclosure has advantages, such as capability of material identification, rapid examination speed, small volume, light weight, portability, low cost, freedom from radiation, and simple maintenance. The method and apparatus according to the present disclosure are suitable for inspection in public places having large number and fast flow of people.

BRIEF DESCRIPTION OF THE DRAWINGS

For a better understanding of the present disclosure, embodiments of the disclosure will be described with reference to the figures, in which.

Figure 1:
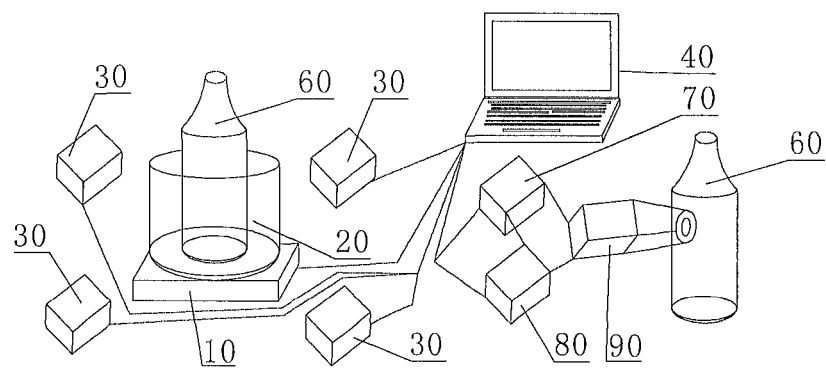
FIG. 1 illustrates a schematic block diagram of an inspection apparatus according to an embodiment of the disclosure.

The figures do not illustrate every circuit or structure in the embodiments. Throughout the figures, identical reference signs refer to identical or similar components or features.

DETAILED DESCRIPTION OF THE EMBODIMENTS

The particular embodiments of the disclosure are described below in detail. It shall be noted that the embodiments herein are used for illustration only, but are not limiting of the disclosure. In the description below, a number of particular details are explained to provide a better understanding of the disclosure. However, it is apparent to those skilled in the art that the disclosure can be implemented without these particular details. In other examples, well-known circuits, materials or methods are not described so as not to obscure the disclosure.

Throughout the specification, reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" occurring at various positions throughout the specification may not refer to one and the same embodiment or example. Furthermore, specific features, structures or properties may be combined into one or several embodiments or examples in any appropriate ways. Moreover, it should be understood by those skilled in the art that figures here are for the purpose of illustration, and not necessarily drawn to scale. It should be appreciated that "connecting" or "coupling" a component to another component may mean that the component is directly connected or coupled to the other component, or there may be a component intervening between them. On the contrary, "directly connecting" or "directly coupling" a component to another component means that there is no intervening component. Like reference signs refer to similar elements throughout the figures. The term "and/or" used herein means any and all combinations of one or more listed items.

In view of a problem with conventional technology, some embodiments of the present disclosure provide a method and apparatus for inspection of liquid, which can combine Raman-spectra-based detection with a technique using an electronic scale and barcode scanning to rapidly examine a liquid under inspection, and determine whether the liquid is safe or dangerous.

Meanwhile, each of the Raman spectra analysis technique and the technique using an electronic scale and barcode scanning can be used independently for material identification of the liquid, which facilitates rapid examination. For example, the Raman spectra analysis technique may be used independently for inspection of the liquid, and the technique using an electronic scale and barcode scanning may also be used independently for inspection of the liquid.

In other embodiments of the disclosure, the package of a liquid is first observed. If the package is made of transparent or semi-transparent material, the Raman spectra analysis technique is used to examine the liquid. Specifically, the transparent or semi-transparent part of the package is aligned with a laser-emitting end of a Raman spectra analysis module. Upon operation, a laser is emitted, and Raman spectra analysis is performed on the liquid. The Raman spectra information of the liquid is compared with standard Raman spectra information of the liquid in a database to obtain an analysis result. Further, material identification may be performed on the liquid.

If the package is opaque, the technique using an electronic scale and barcode scanning is used to examine the liquid. The liquid is placed in or on an electronic scale to obtain weight information of the liquid. A barcode reader reads barcode information of the liquid, and retrieves standard weight information of the liquid from a database based on the read barcode information. Then, the weight information from the electronic scale and the standard weight information from the database are automatically compared to obtain an analysis result.

For a dangerous liquid in an opaque package, liquid without barcode information, or liquid for which the package has been opened and the weight cannot be determined, a method of sampling with a package of transparent material may be used. Then, the Raman spectra analysis technique is used for examination or material identification of the liquid to obtain an analysis result.

FIG. 1 illustrates a schematic block diagram of an inspection apparatus according to an embodiment of the disclosure. As shown in FIG. 1, the inspection apparatus includes: a laser 70 that emits laser; a spectrometer 80 that receives Raman spectra of a liquid; an optical path module 90 that is provided between the laser 70 and the spectrometer 80, and that splits the optical path, causes the laser to arrive at the liquid 60 under inspection, and transmits the Raman spectra of the liquid 60 back to the spectrometer 80; an electronic scale 10 that measures to obtain an actual weight of the liquid 60; a barcode reader 30 that reads a barcode on the liquid 60, and provides it to a computer data processor; and a computer data processor 40 that is coupled with the electronic scale 10 and the barcode reader 30, and that processes data collected by a data collector and outputs an examination result.

In some embodiments, the optical path module 90 may be a probe with or without an optical fiber. In some embodiments, there may be one or more Raman spectra modules each including the above laser, spectrometer, and optical path module. The Raman spectra module is used for rapid inspection of liquid in cooperation with the computer data processor.

As shown in FIG. 1, the barcode reader 30 is disposed around a carrier tray 20. Cables for outputting data collected by the electronic scale 10 and the barcode reader 30 are coupled to the computer data processor 40 in which the collected data are stored. In some embodiments, the electronic scale has one or more weighing sensors. There may be one or more barcode readers. In the case of multiple barcode readers, they may be provided in a uniform or non-uniform arrangement. The computer data processor 40 may be a PC or an embedded processing unit. Further, the computer data processor 40 may use a predefined recognition algorithm for the comparison operation.

Figure 2:
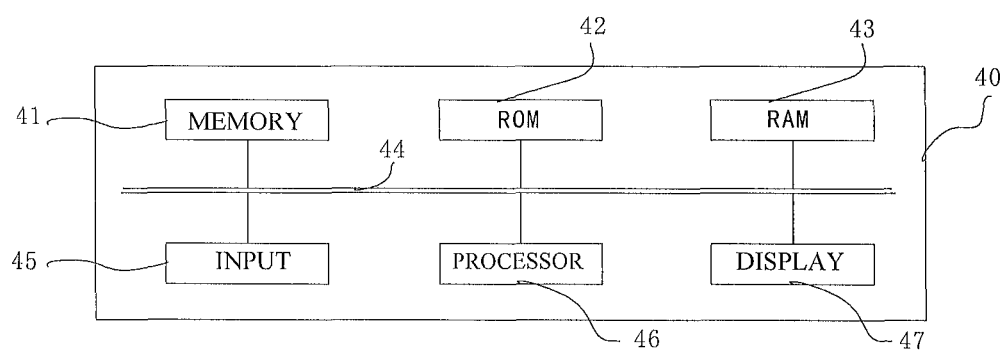
FIG. 2 illustrates a block diagram of a data processor in the inspection apparatus of FIG. 1.

FIG. 2 illustrates a block diagram of the computer data processor 40 in the inspection apparatus of FIG. 1. As shown in FIG. 2, the data collected by the data collector are stored in a memory 41. A Read Only Memory (ROM) 42 stores configuration information and programs for the computer data processor. A Random Access Memory (RAM) 43 stores temporarily various data during operation of the processor 46. The memory 41 may further store computer programs for data processing. An internal bus 44 connects the memory 41, ROM 42, RAM 43, an input device 45, the processor 46, and a display device 47 together.

When a user inputs an operation command via the input device 45, such as via one or more buttons, one or more sensors, or a keyboard and/or mouse, instruction codes in the computer programs instruct the processor to perform predefined data processing algorithms. The obtained result of data processing may be displayed in the display device 47, such as LCD display, or directly outputted in a form of hardcopy.

Figure 3:
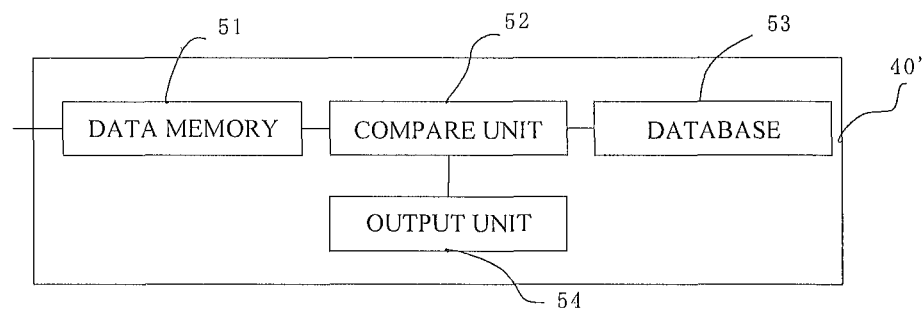
FIG. 3 illustrates a functional block diagram of a computer processor in the inspection apparatus of FIG. 1.

FIG. 2 illustrates a functional block diagram of the computer data processor 40 in the inspection apparatus of FIG. 1. Another example of the computer data processor is shown in FIG. 3. The computer data processor 40' includes: a data memory 51 that stores information about programs, database and the like; a comparison unit 52 that compares the actual weight data from the electronic scale and standard weight data pre-stored in the database to determine identification information of the liquid 60; a database 53 that stores predefined standard weight information and barcode information; and an output unit 54 (e.g., a display or some other type of output device) that outputs the identification information from the comparison unit 52 to an operator.

In some embodiments, the liquid is determined to be suspicious if a difference between the actual weight information and the standard weight information is larger than a first preset threshold, for example, 1% of the weight of the liquid.

In some embodiments, the liquid is determined to be suspicious if a difference between the Raman spectra information of the liquid and the standard Raman spectra information (e.g., a difference of peak values or peak positions) is larger than a second preset threshold.

Figure 4:
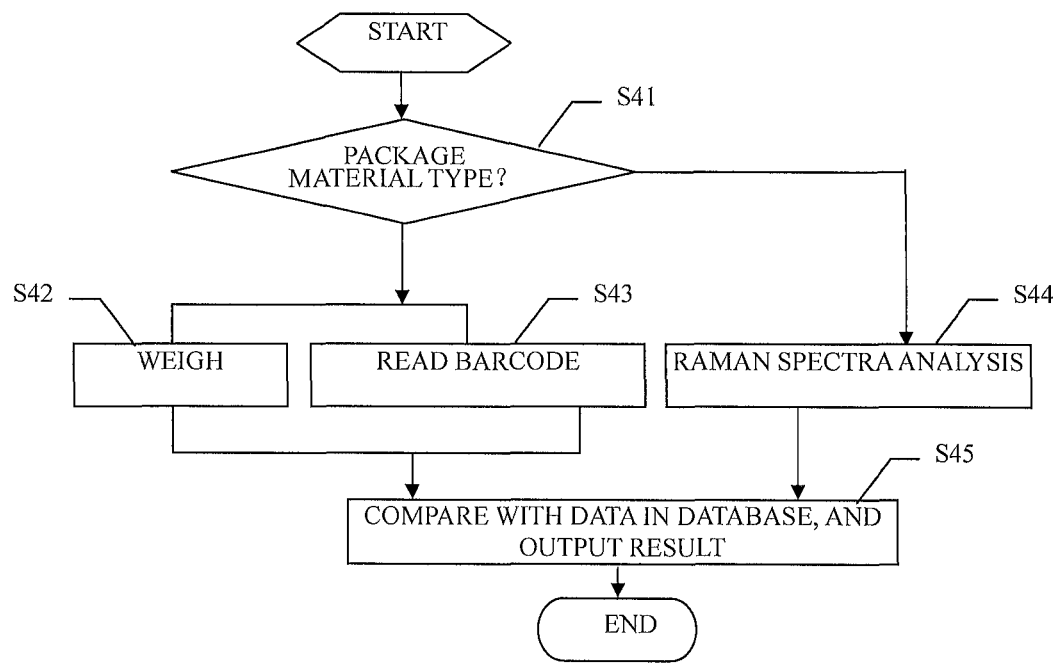
FIG. 4 illustrates a flowchart of an inspection method according to an embodiment of the disclosure.

FIG. 4 illustrates a flowchart of an inspection method according to an embodiment of the disclosure. As shown in FIG. 4, at step S41, the package material of the liquid 60 under inspection is observed for selection of different inspection methods according to the package material. At step S42, if the package material is opaque, the liquid 60 is placed on the carrier tray 20, and the electronic scale automatically measures the weight of the liquid 60. At the same time, at step S43, the barcode reader 30 automatically reads the barcode information of the liquid 60, and the weight information and the barcode information are transmitted to the computer data processor 40. At step S44, if the package material is transparent or semi-transparent, the liquid 60 is placed at the optical path module 90 of the Raman spectrometer for examination, and the examination information is transmitted to the computer data processor 40. At step S45, the computer data processor 40 automatically compares the received data with standard data in the database 53, and displays the comparison result on the output unit 54.

Although the above embodiments described a combination of a Raman spectra technique and a barcode technique, in other embodiments the article under inspection may be directly weighted, and standard weight information may be obtained from a computer based on the barcode on the package for comparison, despite whether the package is transparent or semi-transparent.

Further, in the case that the package of the liquid can be opened or has been opened, part of the liquid may be sampled for Raman spectra inspection. In an example, part of the liquid may be taken out and put into a transparent package. Then, the laser-emitting end of the Raman spectra module is directed at the transparent package. Upon operation, a laser beam is emitted to perform Raman spectra analysis on the part of the liquid. The Raman spectra information of the part of the liquid is compared with the standard Raman spectra information of the liquid in the database to obtain an analysis result of the liquid.

Although the above embodiments are described with combination of the Raman spectra technique and the technique using barcode reader and electronic scale, those skilled in the art will appreciate that the Raman spectra technique and the technique using barcode reader and electronic scale can be used independently to implement the present disclosure.

While the present disclosure has been described with reference to several typical embodiments, it is apparent to those skilled in the art that the terms are used for illustration and explanation purpose and not for limitation. The present disclosure may be practiced in various forms without departing from the esprit or essence of the disclosure. It should be understood that the embodiments are not limited to any of the foregoing details, and shall be interpreted broadly within the esprit and scope as defined by the following claims. Therefore, modifications and alternatives falling within the scope of the claims and equivalents thereof are to be encompassed by the scope of the present disclosure which is defined by the claims as attached.

What is claimed is:

1. A method of inspection of liquids, the method comprising:
    determining whether a package of a liquid is transparent, semi-transparent or opaque;
    when or once the package of the liquid is determined as being transparent or semi-transparent,
        directing a laser-emitting end of a Raman spectra module at the transparent or semi-transparent package of the liquid,
        operating the module to emit a laser beam at the liquid,
        performing Raman spectra analysis on the liquid, and
        comparing Raman spectra information of the liquid with standard Raman spectra information in a database to obtain an analysis result of the liquid; and
    when or once the package of the liquid is determined as being opaque,
        placing the package on an electronic scale to obtain weight information,
        reading barcode information of the package with a barcode reader,
        retrieving standard weight information for the package from a database based on the read barcode information, and
        comparing the weight information from the electronic scale with the standard weight information from the database to determine whether the liquid is dangerous or suspicious.

2. The method according to claim 1, wherein the liquid is determined to be dangerous or suspicious when or once a difference between the weight information and the standard weight information is larger than a preset threshold.

3. The method according to claim 1, wherein when or once one or more selected from: the package of the liquid is determined as opaque and determined as being openable or having been opened, the package is determined not to have a barcode, or the liquid having been determined as being dangerous or suspicious, the method further comprises:
    taking part of the liquid and putting it into a transparent package;
    directing the laser-emitting end of the Raman spectra module at the transparent package;
    operating the Raman spectra module to emit a laser beam at the part of the liquid to perform Raman spectra analysis on the part of the liquid; and
    comparing Raman spectra information of the part of the liquid with the standard Raman spectra information in the database to obtain an analysis result of the liquid.

4. The method according to claim 3, wherein when or once a difference between the Raman spectra information of the liquid and the standard Raman spectra information is larger than a preset threshold, the liquid is determined to be dangerous or suspicious and the material of the liquid is identified.

5. An apparatus comprising:
    an electronic scale configured to measure weight of a package of liquid under inspection;
    a barcode reader configured to read barcode information of the package of liquid;
    a Raman spectra module configured to examine the liquid; and
    a computer data processor coupled with the electronic scale, the barcode reader and the Raman spectra module and configured to:
        when or once the package is determined as being opaque, retrieve standard weight information of the liquid from a database based on the read barcode information, and compare the weight information from the electronic scale with the standard weight information from the database to determine whether the liquid is dangerous or suspicious, and
        when or once the package is determined as being transparent or semi-transparent, cause the Raman spectra module to examine the liquid and compare Raman spectra information of the liquid obtained by the Raman spectra module with standard Raman spectra information in a database to obtain an analysis result of the liquid.

6. The apparatus according to claim 5, wherein the Raman spectra module comprises:
    a laser configured to emit a laser beam to irradiate the liquid and generate Raman spectra;
    a spectrometer configured to receive the Raman spectra of the liquid; and
    an optical path module coupled between the laser and the spectrometer and configured to split the optical path, cause the laser beam to arrive at the liquid, and transmit the Raman spectra to the spectrometer.

7. The apparatus according to claim 5, wherein the liquid is determined to be dangerous or suspicious when or once to a difference between the weight information and the standard weight information is larger than a preset threshold.

8. The apparatus according to claim 5, wherein when or once a difference between the Raman spectra information of the liquid and the standard Raman spectra information is larger than a preset threshold, the liquid is determined to be dangerous or suspicious, and the material of the liquid is identified.

9. The apparatus according to claim 6, wherein the optical path module comprises a probe.

10. The apparatus according to claim 5, wherein there are one or more lasers, spectrometers or optical path modules in the Raman spectra module.

11. The apparatus according to claim 5, wherein the electronic scale comprises one or more weighing sensors.

12. The apparatus according to claim 5, comprising a plurality of barcode readers.

13. The apparatus according to claim 5, wherein the computer data processor comprises a PC or an embedded processing unit.

14. The apparatus according to claim 5, wherein the computer data processor is configured to perform the comparison using a predefined recognition algorithm.

15. A method of inspection of a package, the method comprising:
   determining whether a package is transparent, semi-transparent or opaque;
   when or once the package is determined as being transparent or semi-transparent, causing a Raman spectra examination of the package by a Raman spectra module and comparing Raman spectra information of material in the package obtained by the Raman spectra module, with standard Raman spectra information in a database to obtain an analysis result of the material; and
   when or once the package is determined as being opaque, retrieving standard weight information of the package from a database based on barcode information read by a barcode reader, and comparing weight information obtained from an electronic scale configured to measure the weight of the package with the standard weight information from the database to determine whether the package is dangerous or suspicious.

16. The method according to claim 15, wherein when or once one or more selected from: the package is determined as opaque and determined as being openable or having been opened, the package is being determined not to have a barcode, or the package having been determined as being dangerous or suspicious, the method further comprises:
   obtaining Raman spectra information of a part of the material in the package that has been placed into a transparent package; and
   comparing the Raman spectra information of the part of the material with the standard Raman spectra information in the database to obtain an analysis result of the material.

17. The method according to claim 15, wherein when or once a difference between the Raman spectra information of the material and the standard Raman spectra information is larger than a preset threshold, the material is determined to be dangerous or suspicious and the material is identified.

18. A non-transitory computer-readable medium comprising instructions configured to cause a hardware computer processor to:
   when or once a package under inspection and containing liquid, is determined as being opaque, retrieve standard weight information of the liquid from a database based on barcode information read by a barcode reader, and compare weight information obtained from an electronic scale configured to measure the weight of the package with the standard weight information from the database to determine whether the liquid is dangerous or suspicious, and
   only when or once the package of the liquid is determined as being transparent or semi-transparent, cause a Raman spectra examination of the liquid by a Raman spectra module and compare Raman spectra information of the liquid obtained by the Raman spectra module, with standard Raman spectra information in a database to obtain an analysis result of the liquid.

19. The non-transitory computer-readable medium of claim 18, wherein the instructions are further configured to cause a hardware computer processor, when or once to one or more selected from: the package is determined as opaque and determined as being openable or having been opened, the package is determined not to have a barcode, or the liquid having been determined as being dangerous or suspicious:
   obtain Raman spectra information of a part of the liquid in the package that has been placed into a transparent package; and
   compare the Raman spectra information of the part of the liquid with the standard Raman spectra information in the database to obtain an analysis result of the material.

20. The non-transitory computer-readable medium of claim 18, wherein the instructions are further configured to cause a hardware computer processor, when or once a difference between the Raman spectra information of the material and the standard Raman spectra information is larger than a preset threshold, identify liquid as being dangerous or suspicious and identify material of the liquid.

* * * * *